(12) United States Patent
Ikemoto

(10) Patent No.: US 11,207,344 B2
(45) Date of Patent: Dec. 28, 2021

(54) SOLUBILIZATION ENHANCER FOR PYRROLOQUINOLINE QUINONE, COMPOSITION COMPRISING SAME AND METHOD FOR ENHANCING SOLUBILIZATION

(71) Applicant: MITSUBISHI GAS CHEMICAL COMPANY, INC., Chiyoda-ku (JP)

(72) Inventor: Kazuto Ikemoto, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 16/758,668

(22) PCT Filed: Sep. 14, 2018

(86) PCT No.: PCT/JP2018/034120
§ 371 (c)(1),
(2) Date: Apr. 23, 2020

(87) PCT Pub. No.: WO2019/082549
PCT Pub. Date: May 2, 2019

(65) Prior Publication Data
US 2020/0352981 A1    Nov. 12, 2020

(30) Foreign Application Priority Data

Oct. 25, 2017  (JP) .............................. JP2017-206348

(51) Int. Cl.
*A61K 31/716* (2006.01)
*A61K 47/22* (2006.01)
*A61K 9/00* (2006.01)
*A61K 47/02* (2006.01)

(52) U.S. Cl.
CPC .......... *A61K 31/716* (2013.01); *A61K 9/0095* (2013.01); *A61K 47/02* (2013.01); *A61K 47/22* (2013.01)

(58) Field of Classification Search
None
See application file for complete search history.

(56) References Cited

U.S. PATENT DOCUMENTS

| 5,505,981 A * | 4/1996 | Wakabayashi ......... A21D 2/186 426/658 |
| 10,568,345 B2 * | 2/2020 | Wakabayashi ............ A23L 2/58 |
| 2010/0061969 A1 * | 3/2010 | Otsubo .................. A23L 33/12 424/94.1 |
| 2015/0182579 A1 | 7/2015 | Hageman |
| 2016/0075700 A1 | 3/2016 | Ikemoto |

FOREIGN PATENT DOCUMENTS

| JP | 2012-180319 A | 9/2012 |
| JP | 2014-14354 A | 1/2014 |
| JP | 2014-84302 A | 5/2014 |
| JP | 2014-161295 A | 9/2014 |
| JP | 2015-92875 A | 5/2015 |
| JP | 2016-174552 A | 10/2015 |
| JP | 2016-106109 A | 6/2016 |
| WO | WO2014/007606 A1 | 1/2014 |

OTHER PUBLICATIONS

Kajita, T. et al., "Sitology Dictionary of Food Preparation," Asakura Publishing Co., Ltd., 1996, total pages: 2.
Okuma, K. et al., "Development of Indigestible Dextrin," Journal of Appl. Glycosci. 2006, vol. 53, pp. 65-69.
Akagawa M. et al., "Recent progress in studies on the health benefits of Pyrroloquinoline quinone," 2016, Bioscience, Biotechnology, and Biochemistry, vol. 80, No. 1, pp. 13-22.
International Search Report dated Dec. 4, 2018 in PCT/JP2018/034120 filed on Sep. 14, 2018, 3 pages.

* cited by examiner

*Primary Examiner* — Dale R Miller
(74) *Attorney, Agent, or Firm* — Oblon, McClelland, Maier & Neustadt, L.L.P.

(57) ABSTRACT

Provided is a solubilization enhancer for pyrroloquinoline quinone or a salt thereof in an aqueous solvent, comprising resistant dextrin as an active ingredient.

6 Claims, No Drawings

SOLUBILIZATION ENHANCER FOR PYRROLOQUINOLINE QUINONE, COMPOSITION COMPRISING SAME AND METHOD FOR ENHANCING SOLUBILIZATION

TECHNICAL FIELD

The present invention relates to a solubilization enhancer for pyrroloquinoline quinone, a composition comprising the same and a method for enhancing solubilization.

BACKGROUND ART

Resistant dextrin, a kind of dietary fiber, is known to have an effect of regulating the functions of the intestines, an effect of suppressing the elevation of blood sugar levels, and an effect of suppressing the elevation of neutral fat levels. The resistant dextrin is added to various foods including soft drinks (see, for example, Patent Literatures 1 and 2).

Resistant dextrin needs to be ingested on a gram scale per day in order to exert the functions described above (see, for example, Non Patent Literature 1).

Pyrroloquinoline quinone is known to have functions such as improvement in brain function, life extension, and moisturization of the skin. Pyrroloquinoline quinone is usually provided as disodium salt, and needs to be ingested on a scale of several tens of milligrams per day for improvement in brain function or moisturization of the skin (see, for example, Non Patent Literature 2).

CITATION LIST

Patent Literature

Patent Literature 1: Japanese Patent Laid-Open No. 2014-014354
Patent Literature 2: Japanese Patent Laid-Open No. 2014-161295

Non Patent Literature

Non Patent Literature 1: Journal of Applied Glycoscience, Vol. 53 (2006), No. 1, p. 65-69
Non Patent Literature 2: Biosci Biotechnol Biochem. 2016; 80 (1): 13-22. doi:10.1080/09168451.2015.1062715.

SUMMARY OF INVENTION

Technical Problem

Owing to rising health consciousness in recent years, the number of soft drinks supplemented with food materials having heath functionality is increasing yearly in order to add health values thereto. However, pyrroloquinoline quinone has the disadvantages of having low solubility in an aqueous solvent and being easily deposited. Particularly, in the case of including hard water (calcium or magnesium), the solubility is decreased. The solubility of pyrroloquinoline quinone also varies depending on pH in an aqueous solution, and pyrroloquinoline quinone tends to be deposited at acidic pH.

An object of the present invention is to provide an approach that can reduce the deposition of pyrroloquinoline quinone in an aqueous solvent.

Solution to Problem

Under these circumstances, the present inventors have found that the solubility of pyrroloquinoline quinone, which is a food material having health functionality, in an aqueous solution is increased in the presence of resistant dextrin.

Specifically, the present invention encompasses the following aspects of the invention.

(1)
A solubilization enhancer for pyrroloquinoline quinone or a salt thereof in an aqueous solvent, comprising resistant dextrin as an active ingredient.
(2)
The solubilization enhancer according to (1), wherein the solubilization enhancer is in a powder form.
(3)
A composition comprising a solubilization enhancer according to (1) or (2).
(4)
The composition according to (3), wherein a content of the resistant dextrin is 0.3 to 23% by weight.
(5)
The composition according to (3) or (4), wherein the composition is in a food or beverage form.
(6)
The composition according to any of (3) to (5), wherein the composition is in a beverage form, and pH thereof is 1.5 to 8.
(7)
The composition according to (6), wherein the aqueous solvent is hard water.
(8)
The composition according to (6) or (7), comprising carbon dioxide gas.
(9)
A method for enhancing the solubilization of pyrroloquinoline quinone or a salt thereof, comprising the step of bringing the pyrroloquinoline quinone or the salt thereof into contact with resistant dextrin in an aqueous solvent.

Advantageous Effects of Invention

The present invention can provide a solution containing a high concentration of pyrroloquinoline quinone rich in physiological functions by using resistant dextrin.

Particularly, hard water is preferred because of containing mineral, but facilitates depositing pyrroloquinoline quinone. Thus, the quality of hard water containing pyrroloquinoline quinone is usually difficult to retain over a long period. According to the present invention, the solubility of pyrroloquinoline quinone is increased by the addition of resistant dextrin, irrespective of whether to be soft water or hard water. Therefore, the quality of an aqueous solution containing pyrroloquinoline quinone can be retained over a long period.

DESCRIPTION OF EMBODIMENTS

Hereinafter, the mode for carrying out the present invention (hereinafter, referred to as the "present embodiment") will be described in detail. The following embodiments are given for merely illustrating the present invention, and the present invention is not limited by only the embodiment.

The solubilization enhancer according to the first embodiment contains resistant dextrin as an active ingredient. The solubilization enhancer may be constituted of the resistant dextrin alone.

The resistant dextrin according to the present embodiment is water-soluble dietary fiber obtained by acidifying and/or heating starch derived from a plant such as corn, wheat, rice, beans, tubers and roots, or tapioca, treating the obtained roasted dextrin with a amylase and/or glucoamylase according to the need, followed by desalting and decolorization according to the need, and is characterized by being resistant. This resistant dextrin can be obtained, for example, by adding a trace amount of hydrochloric acid to starch, and heating and enzymatically treating the mixture, and refers to, for example, dextrin comprising a resistant component, preferably dextrin comprising 85 to 95% by weight of a resistant component, measured by high-performance liquid chromatography (enzyme-HPLC) which is a method for analyzing dietary fiber as described in Notice No. 13, Office of Health Policy for Newly-Developed Foods, Life Sanitation Bureau, Ministry of Health and Welfare ("Analytical Methods for Nutrition Labeling in Japan"). In the present embodiment, a reduction product thereof produced by hydrogenation is also included in the resistant dextrin. Commercially available products can be used as the resistant dextrin and the reduction product thereof (reduced resistant dextrin).

The pyrroloquinoline quinone (hereinafter, also referred to as "PQQ") targeted by the solubilization enhancer is a substance having a structure represented by the general formula (1).

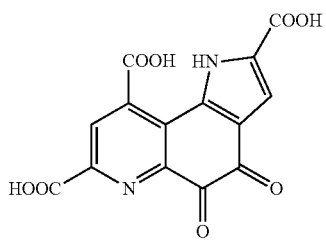

Formula 1

PQQ is often used as an alkali metal salt. Salts having one to three alkali metal ions attached are known. The alkali metal salt is preferably sodium or potassium salt, more preferably disodium salt.

The solubility of pyrroloquinoline quinone in an aqueous solvent varies depending on the hardness of the aqueous solvent or the temperature or pH of a solution at the time of dissolution. The "solubilization enhancement" used herein means that the solubility of pyrroloquinoline quinone is larger than that in the case of adding no active ingredient, when compared under the same conditions except for the addition of the active ingredient.

The form of the solubilization enhancer of the present embodiment may be a powder. The resistant dextrin is water-soluble dietary fiber and is dissolved in an aqueous solvent. The "aqueous solvent" used herein means a solvent such as an aqueous phase, an alcohol phase or a mixed phase thereof. Examples thereof include water, soft drinks, alcohols, and fruit juice beverages. The content of the resistant dextrin in the aqueous solvent can be determined in consideration of the concentration of pyrroloquinoline quinone in a final product. Since the solubility of pyrroloquinoline quinone varies depending on the hardness or temperature of the aqueous solvent, or the temperature or pH of a solution at the time of dissolution, these factors must also be taken into consideration for determining the amount of the resistant dextrin added.

The composition according to the second embodiment comprises the solubilization enhancer. The composition may be in a food or beverage form, preferably in a food or beverage form.

The amount of the resistant dextrin in the composition is determined in consideration of the desired solubility of pyrroloquinoline quinone. In the case of dissolving pyrroloquinoline quinone at 2 g/L or more in soft water of pH 3 to 4 at 4° C., the composition of the present embodiment preferably contains 0.3 to 23% by weight, more preferably 0.5 to 15% by weight, further preferably 0.5 to 10% by weight, of the resistant dextrin, though the amount is not intended to be limited thereto. Less than 0.3% by weight of the resistant dextrin also has a solubilization enhancing effect, whereas a concentration lower than this concentration is low effective.

Usually, the concentration of PQQ or a salt thereof in a beverage is appropriately adjusted within the range of 1 to 20 g/L. The resistant dextrin can improve the solubility of pyrroloquinoline quinone by nearly 3 times when compared under the same conditions, and can therefore be suitably blended into a food or beverage containing a high concentration of pyrroloquinoline quinone.

The resistant dextrin is water-soluble dietary fiber and is dissolved in an aqueous vehicle. Hence, the form of the solubilization enhancer to be blended into the composition may be a powder. When the pyrroloquinoline quinone is also a powder, the weight ratio of resistant dextrin:pyrroloquinoline quinone and/or a salt thereof to be blended into the composition is appropriately adjusted within the range of 1:1 to 10000:1, preferably 1:20.

When the composition is a beverage, the pH thereof is preferably 1.5 to 8. Since pyrroloquinoline quinone tends to be precipitated at acidic pH, the solubilization enhancer is particularly effective for an acidic beverage used as the composition. The aqueous solvent constituting the beverage is preferably soft water from the viewpoint of improvement in the solubility of pyrroloquinoline quinone, but may be hard water.

When the composition is a food or beverage, a component such as a sweetener, an acidulant, an inorganic salt, an organic acid salt, an amino acid, a protein, a nucleic acid, a flavor, or a preservative may be appropriately blended thereinto. When the composition is, for example, a beverage such as a soft drink, a sweetener, particularly, a high-intensity sweetener is often blended thereinto.

The high-intensity sweetener means a material that can impart sufficient sweetness to a food by addition in a small amount because the sweetness perceived when the material is put in the mouth in the same amount (mass) as that of sucrose is higher by several tens to several thousands of times than that of sucrose, among food additives that are used for the purpose of imparting sweetness to foods.

The high-intensity sweetener to be added may be a natural high-intensity sweetener or may be a synthetic high-intensity sweetener. Examples thereof include aspartame, acesulfame potassium, xylitol, D-xylose, glycyrrhizin and acids and salts thereof, saccharin, saccharin sodium, sucralose, D-sorbitol, *stevia* extracts, *stevia* powders, thaumatin, abrusoside A, cyclocarioside I, N-acetylglucosamine, L-arabinose, oligo-N-acetylglucosamine, licorice extracts, α-glucosyltransferase-treated *stevia*, enzymatically treated licorice, L-sorbose, neotame, Siraitia grosvenorii extracts, L-rhamnose, and D-ribose.

The high-intensity sweetener to be added may be used as a single component, or two or more of the high-intensity sweeteners may be used in combination. Preferably, the high-intensity sweetener may consist of one or two or more members selected from the group consisting of acesulfame potassium, sucralose, *stevia*, aspartame and neotame. In the case of using two or more high-intensity sweeteners in combination, the amount of the high-intensity sweeteners can be indicated by an amount obtained by summing up the respective amounts of the two or more high-intensity sweeteners.

The high-intensity sweetener used may be a commercially available product or may be produced according to a method known in the art. The high-intensity sweetener used may be an extract of a plant or the like containing the high-intensity sweetener of interest (e.g., for *stevia*, a *stevia* extract).

The content of the high-intensity sweetener in the composition of the present embodiment can be appropriately determined according to the beverage of interest. Depending on the degree of sweetness, the content of the high-intensity sweetener may be in the range of, for example, 0.01 to 0.2% by weight.

A combination of aspartame, acesulfame potassium and sucralose is possible as the high-intensity sweetener.

The composition of the present embodiment may be a carbonated beverage. Examples of the carbonated beverage include cider beverages, soda pop beverages, cola beverages, fruit juice-containing carbonated beverages, and non-alcoholic beer type beverages.

When the composition of the present embodiment is a beverage, the container thereof is appropriately determined according to the type of a final product. Examples of such a container include PET bottles, cans, and bottles.

A preferred form exploiting the composition of the present embodiment is a beverage containing pyrroloquinoline quinone and resistant dextrin. A concentrate can be formed according to the composition of the present invention and facilitates production.

The method for enhancing the solubilization of pyrroloquinoline quinone or a salt thereof according to the third embodiment comprises the step of bringing the pyrroloquinoline quinone into contact with resistant dextrin in an aqueous solvent. This method can be used in a method for producing a beverage containing a high concentration of pyrroloquinoline quinone.

For the resistant dextrin and the pyrroloquinoline quinone for use in the methods of these embodiments, and the manners of addition thereof, see the items described above.

EXAMPLES

Hereinafter, the present invention will be described in more detail with reference to Examples. However, the present invention is not limited by Examples given below.

The pyrroloquinoline quinone disodium salt used in the present Examples was BioPQQ manufactured by Mitsubishi Gas Chemical Co., Inc. Absorbance was calculated using an ultraviolet-visible spectrometer.

Examples 1 to 6 and Comparative Examples 1 and 2 Dissolution in Water (pH 3 to 4)

Resistant dextrin (manufactured by Daito Bussan Co., Ltd.) was dissolved in ion-exchange water so as to attain the predetermined concentrations shown in Table 1. 1 ml of this solution was mixed with 10 mg of pyrroloquinoline quinone disodium salt to obtain aqueous solutions. The obtained aqueous solutions were placed at 4° C. and 25° C. After 20 hours, undissolved pyrroloquinoline quinone disodium salt was removed by centrifugation. Each aqueous solution was diluted with a phosphate buffer, and the solubility of the pyrroloquinoline quinone disodium salt in water was calculated by absorbance measurement. The solubility of the pyrroloquinoline quinone disodium salt in water without the addition of the resistant dextrin in Comparative Example 1 is defined as 100. The obtained values are shown in Table 1. The solubility of the pyrroloquinoline quinone disodium salt in water in Comparative Example 1 was 1.8 g/L (4° C.) and 2.99 g/L (25° C.)

Results of conducting a test using dextrin hydrate (manufactured by Wako Pure Chemical Industries, Ltd.) in Comparative Example 2 are also shown in Table 1. The weight ratio between resistant dextrin and pyrroloquinoline quinone described in the tables is the weight ratio between the resistant dextrin and the pyrroloquinoline quinone disodium salt used as raw materials.

TABLE 1

|  | Resistant dextrin concentration (% by weight) | Weight ratio of resistant dextrin:pyrroloquinoline quinone | Relative value of solubility (4° C.) (g/L) | Absolute value of solubility (4° C.) | Relative value of solubility (25° C.) | Absolute value of solubility (25° C.) (g/L) |
|---|---|---|---|---|---|---|
| Example 1 | 0.5 | 1:2 | 122 | 2.20 | 130 | 3.89 |
| Example 2 | 1 | 1:1 | 122 | 2.20 | 130 | 3.89 |
| Example 3 | 2 | 2:1 | 140 | 2.52 | 130 | 3.89 |
| Example 4 | 5 | 5:1 | 140 | 2.52 | 130 | 3.89 |
| Example 5 | 10 | 10:1 | 144 | 2.59 | 140 | 4.19 |
| Example 6 | 20 | 20:1 | 117 | 2.11 | 157 | 4.69 |
| Comparative Example 1 | 0 | 0:1 | 100 | 1.8 | 100 | 2.99 |
| Comparative Example 2 | 0 (5% by weight of dextrin hydrate) | — | 101 | 1.8 | 94 | 2.81 |

The effect of enhancing the solubility of pyrroloquinoline quinone was not observed in usual dextrin, demonstrating that the effect of solubilizing pyrroloquinoline quinone is an effect specific for resistant dextrin.

Examples 7 to 10 and Comparative Example 3 Hard Water

The solubility of pyrroloquinoline quinone disodium salt in a 0.2 g/L aqueous calcium chloride solution (U.S. hardness: 180 mg/L) as a model having increased hardness instead of water was measured at 4° C. or 25° C. in the same way as in Example 1. The concentration of resistant dextrin in each aqueous solution was as shown in Table 2. The solubility of the pyrroloquinoline quinone disodium salt in the aqueous calcium chloride solution in Comparative Example 3 was 1.6 g/L (4° C.) and 2.83 g/L (25° C.)

TABLE 2

|  | Resistant dextrin concentration (% by weight) | Weight ratio of resistant dextrin:pyrroloquinoline quinone | Relative value of solubility (4° C.) | Absolute value of solubility (4° C.) (g/L) | Relative value of solubility (25° C.) | Absolute value of solubility (25° C.) (g/L) |
|---|---|---|---|---|---|---|
| Example 7 | 1 | 1:1 | 146 | 2.34 | 147 | 4.16 |
| Example 8 | 5 | 5:1 | 158 | 2.53 | 147 | 4.16 |
| Example 9 | 10 | 10:1 | 227 | 3.63 | 155 | 4.39 |
| Example 10 | 20 | 20:1 | 268 | 4.29 | 194 | 5.49 |
| Comparative Example 3 | 0 | 0:1 | 100 | 1.6 | 100 | 2.83 |

As is evident from the results of Table 2, the present invention can exert effects not only in soft water but in hard water. Although the solubility of pyrroloquinoline quinone in hard water is decreased, the present invention can also be used in a mineral-strengthened beverage by combined use with resistant dextrin.

Examples 11 to 14 and Comparative Example 4
Effect at Acidic pH (pH 2)

The solubility of pyrroloquinoline quinone disodium salt in an aqueous solution containing 1% by weight of citric acid instead of water was measured at 25° C. in the same way as in Example 1. The concentration of resistant dextrin in each aqueous solution was as shown in Table 3.

TABLE 3

|  | Resistant dextrin concentration (% by weight) | Weight ratio of resistant dextrin:pyrroloquinoline quinone | Relative value of solubility (25° C.) | Absolute value of solubility (25° C.) (g/L) |
|---|---|---|---|---|
| Example 11 | 1 | 1:1 | 117 | 2.10 |
| Example 12 | 5 | 5:1 | 173 | 3.11 |
| Example 13 | 10 | 10:1 | 184 | 3.31 |
| Example 14 | 20 | 20:1 | 346 | 6.23 |
| Comparative Example 4 | 0 | 0:1 | 100 | 1.8 |

The solubility of the pyrroloquinoline quinone disodium salt in water in Comparative Example 4 was 1.8 g/L (25° C.)

Example 15 and Comparative Example 5 Effect at Neutral pH (pH 7)

30 mg of pyrroloquinoline quinone disodium salt was added to 1 ml of water, and its pH was adjusted to 7 using sodium hydroxide. The solubility of pyrroloquinoline quinone disodium salt was measured at 25° C. in the same way as in Example 1. The concentration of resistant dextrin in each aqueous solution was as shown in Table 4.

TABLE 4

|  | Resistant dextrin concentration (% by weight) | Weight ratio of resistant dextrin:pyrroloquinoline quinone | Relative value of solubility (25° C.) | Absolute value of solubility (25° C.) (g/L) |
|---|---|---|---|---|
| Example 15 | 10 | 10:3 | 170 | 26.5 |
| Comparative Example 5 | 0 | 0:3 | 100 | 15.6 |

The solubility of the pyrroloquinoline quinone disodium salt in water in Comparative Example 5 was 15.6 g/L (25° C.)

The present invention can provide a composition comprising pyrroloquinoline quinone without precipitation by blending with resistant dextrin, and by extension, a composition containing a high concentration of pyrroloquinoline quinone.

The invention claimed is:

1. A composition, comprising resistant dextrin and pyrroloquinoline quinone or a salt thereof, wherein the resistant dextrin is present at 0.3 to 23% by weight relative to a total weight of the composition.

2. The composition of claim 1, wherein the composition is in a food or beverage form.

3. The composition of claim 1, wherein the composition is in a beverage form, and wherein a pH of the composition is from 1.5 to 8.

4. The composition of claim 3, wherein an aqueous solvent is present, and the aqueous solvent is hard water.

5. The composition of claim 3, further comprising carbon dioxide gas.

6. A method for enhancing the solubilization of pyrroloquinoline quinone or a salt thereof, the method comprising: contacting pyrroloquinoline quinone or a salt thereof with resistant dextrin in an aqueous solvent.

* * * * *